United States Patent
Silberg

[11] Patent Number: 5,980,512
[45] Date of Patent: Nov. 9, 1999

[54] ENHANCED LASER SKIN TREATMENT MECHANISM

[76] Inventor: Barry Silberg, 1111 Sonoma Ave Ste 210, Santa Rosa, Calif. 95405

[21] Appl. No.: 09/031,383

[22] Filed: Feb. 26, 1998

[51] Int. Cl.⁶ .................................................. A61B 17/36
[52] U.S. Cl. ................................... 606/9; 606/10; 606/13
[58] Field of Search .................................. 606/9, 10, 11, 606/13

[56] References Cited

U.S. PATENT DOCUMENTS

| | | | |
|---|---|---|---|
| 4,638,800 | 1/1987 | Michel | 606/10 |
| 4,784,135 | 11/1988 | Blum et al. | 606/9 |
| 5,057,104 | 10/1991 | Chess | 606/9 |
| 5,188,631 | 2/1993 | L'Esderance, Jr. | 606/5 |
| 5,244,462 | 9/1993 | Delahuerga et al. | 606/42 |
| 5,549,663 | 8/1996 | Cottone, Jr. | 606/195 |
| 5,749,895 | 5/1998 | Sawyer et al. | 606/8 |
| 5,782,249 | 7/1998 | Weber et al. | 606/10 |

Primary Examiner—John P. Leubecker
Attorney, Agent, or Firm—Mark E. Ogram P.C.

[57] ABSTRACT

A surgical apparatus particularly adapted for use in the cosmetic surgery field of skin resurfacing in which a laser is directed towards the imperfection of the skin. The surgical site is bathed with an inert or noble gas which has the affect of replacing the oxygen in the surgical site. Without the oxygen, burning of the surrounding tissue from the laser is minimized. This results in a reduced recuperation time and less pain associated with the procedure. In one embodiment of the invention, a "basin" is created to hold the inert gas; in another embodiment, the inert gas is "sprayed" in line with the laser against the surgical site. In yet another embodiment of the invention, the surgical site is encapsulated and the inert gas in inserted into the capsule. A window in the capsule permits the laser to be used in the now oxygen poor environment within the capsule. Once the surgery is completed, the inert gas is removed from the capsule and a sterile gas adapted to encourage healing (i.e. an oxygen rich gas), in injected into the capsule.

15 Claims, 3 Drawing Sheets

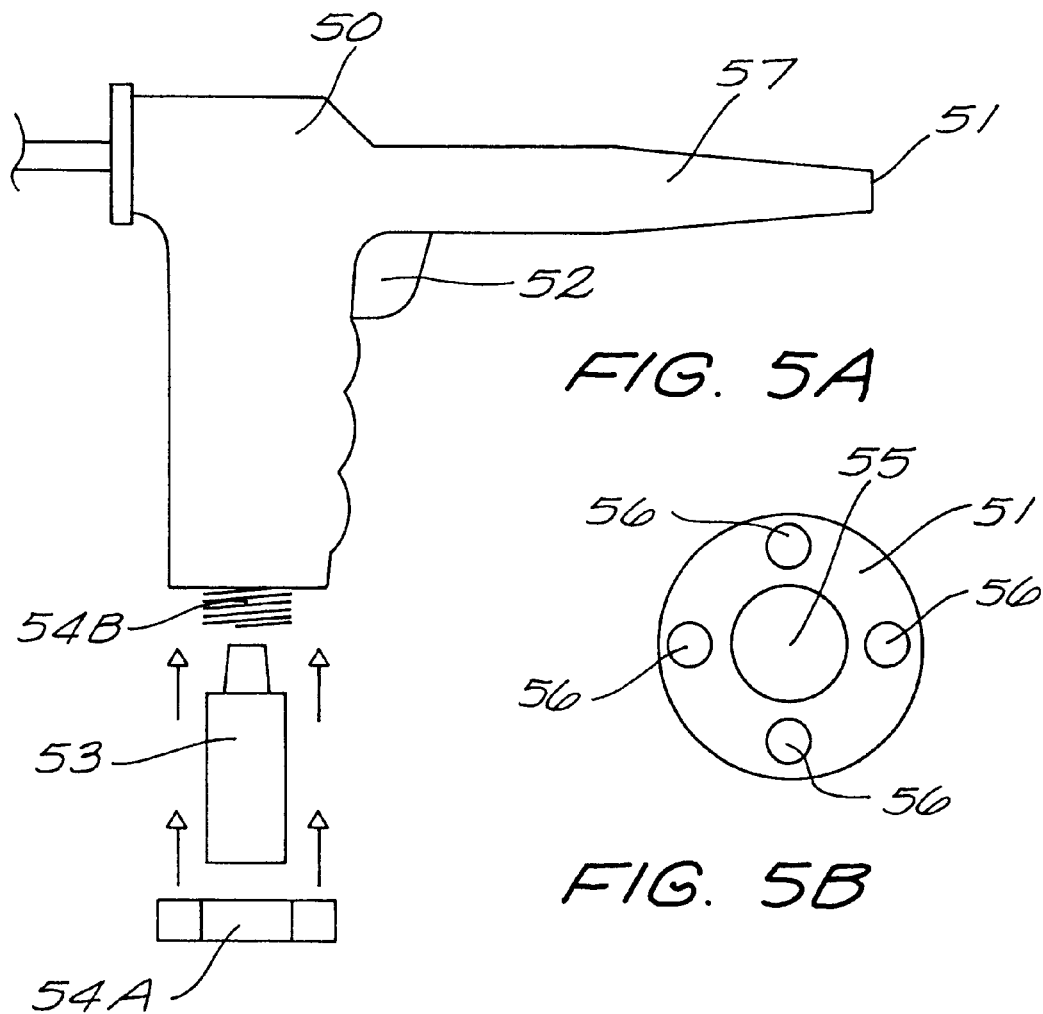
FIG. 5A
FIG. 5B
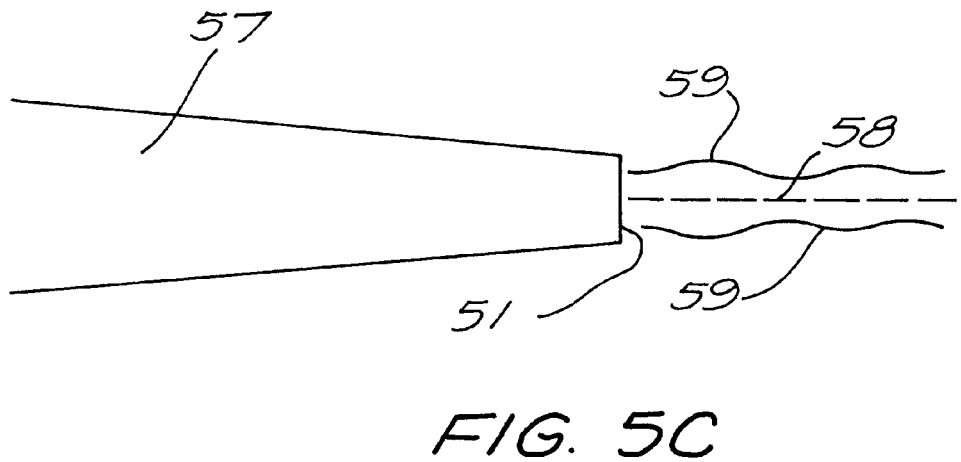
FIG. 5C

ENHANCED LASER SKIN TREATMENT MECHANISM

BACKGROUND

This invention relates generally to surgical techniques and more particularly to the treatment of skin using a laser.

Each year, a vast number of cosmetic treatments of skin imperfections are preformed. These procedures treat a wide variety of skin imperfections ranging from age lines to birth marks, from tattoos to scar tissue. The mode of treatment of these imperfections falls generally into three different categories: abrasion, chemical peeling, and laser treatment.

Abrasion involves physically abrading of the skin tissue to remove the affected tissue. A variety of mechanisms are applied including grinding wheels and files. While these techniques work in general, they often create their own scars and are further extremely painful or uncomfortable for the patient.

Further, in many applications (i.e. strawberry birthmarks), the amount of abrading which must be performed is so extensive that, to perform the procedure with any success, almost the entire skin layer must be removed.

Chemical treatments are easier to control and are used generally for treating an upper layer of the skin. In general, the chemicals applied kill the upper layer of cells which are then sloughed. The treatment though is applied to a wide area, not just the affected tissue, so recuperation is extended. Further, is not finely controlled, the chemical treatment can "burn" the patient and cause further scarring.

Because of the drawbacks to the above two methods, laser treatment of skin disorders has quickly become the method of choice. In this modality, the laser beam is directed against the disorder itself. Due to the heat generated by the laser beam, the beam kills the cells. These cells are either vaporized immediately by the laser beam or are sloughed later.

While the laser beam has a fine focal point and ancillary damage is minimized, the beam does cause some excessive heating of the site which damages the surrounding "good" or healthy cells. This damage creates a heightened discomfort and extends the time required for recuperation.

Further, during the procedure, an excessive amount of smoke is created which obscures the surgical site.

It is clear that there is a need to decrease the secondary damage caused by laser treatment of the skin.

SUMMARY OF THE INVENTION

Within the present invention, a surgical apparatus is created which is particularly adapted for use in the cosmetic field of skin resurfacing in which a laser beam is directed against the imperfection of the skin.

The surgical apparatus of this invention performs at least two different operations: (1) the surgical site is bathed with an oxygen replacing gas such as argon; and, (2) a laser is directed against the surgical site to treat the skin imperfection. Since the oxygen at the site is eliminated, secondary damage created by the heat from the laser is minimized and the amount of smoke which is generated is vastly reduced.

In the first step, the surgical site is bathed with an inert or noble gas which has the affect of replacing the oxygen in the surgical site. Inert or noble gases are any gases in group 0 of the periodic table of the elements. They are monatomic and, with few exceptions, are chemically inert. For this reason, they are ideal for the present invention's use.

The preferred gas is argon. Argon is a colorless, odorless, tasteless, monatomic gas which is not know to combine chemically with any elements. It is used to replace the oxygen proximate to the surgical site. In some applications, helium is also used. Helium must be contained or encapsulated around the surgical site to prevent it from escaping into the atmosphere.

Without the oxygen, burning of the surrounding tissue from the laser is minimized. This results in a reduced recuperation time and less pain associated with the procedure. Further, smoke from the procedure is greatly reduced; thereby providing greater visibility with increased effectiveness of the procedure.

In one embodiment of the invention, a "basin" is created to hold the inert gas; in another embodiment, the inert gas is "sprayed" in line with the laser against the surgical site. This later embodiment is particularly well suited to maintain a suitable layer of the inert gas proximate to the site.

The preferred basin is ring-shaped having a diameter much greater than the surgical site. A lower portion of the basin is equipped with an adhesive so that the basin is firmly, and tightly, secured to the patient prior to the procedure. A rim around the edge of the basin is adapted to maintain the inert gas, such as argon, over the surgical site.

In yet another embodiment of the invention, the surgical site is encapsulated and the inert gas in inserted into the capsule. In this embodiment, a dome or other such structure is secured to the patient to enclose the surgical site. The inert gas, such as argon or helium, is injected into the dome.

A window in the dome allows the laser beam to penetrate and treat the surgical site. Those of ordinary skill in the art readily recognize a variety of materials which can be used as a window for the laser.

A window in the capsule permits the laser to be used in the now oxygen poor environment within the capsule.

Once the treatment has been conducted, the inert gas is washed from within the dome, and in one embodiment, the dome is then filled with a gas which is intended to encourage healing of the surgical site. While a variety of gases are available for this purpose, the preferred gas is oxygen rich allowing the cells to quickly recuperate.

The invention, together with various embodiments thereof, will be fully explained by the accompanying drawings and the following description.

DRAWINGS IN BRIEF

FIG. 5A, 5B, and 5C are various views of an alternative handheld embodiment in which the reservoir of inert gas is secured in the handheld embodiment.

DRAWINGS IN DETAIL

Figure 1:
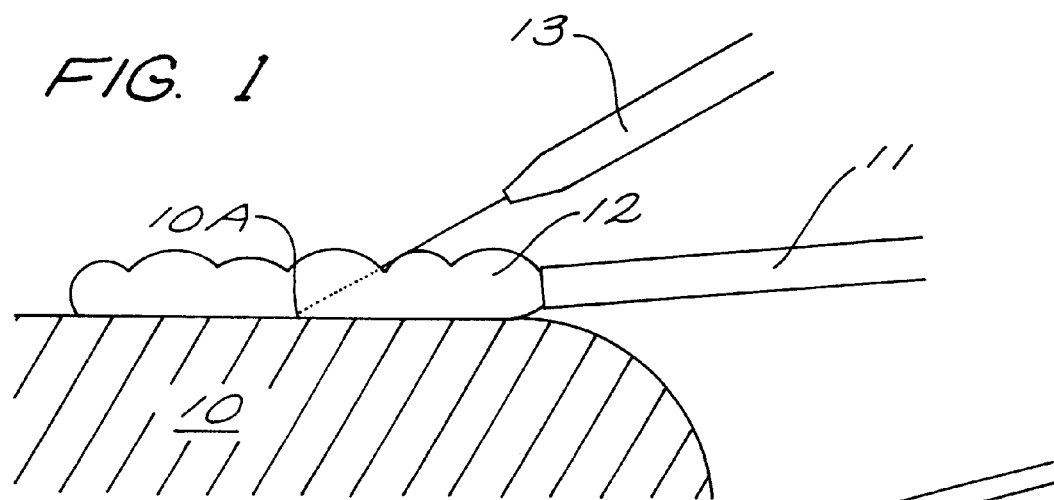
FIG. 1 is a side view of the preferred embodiment of the invention.

FIG. 1 is a side view of the preferred embodiment of the invention. Surgical site 10A on patient 10 is to be treated for a skin imperfection. The combination includes gas dispenser 11 which emits an inert or noble gas 12 which bathes surgical site 10A. This bathing action forces the oxygen from the surgical site. Laser 13 emits a laser beam which is directed against the surgical site 10A. The laser beam treats the skin disorder in an oxygen free or an oxygen lean environment. Heat from the laser beam is not allowed to combine with oxygen to create ancillary burning of the surrounding tissue, only the skin disorder itself is treated.

A further benefit of this procedure is that only minimal smoke is generated. Surgical site 10A remains clearly visible to the surgeon so that the treatment becomes much more exact.

Figure 2:
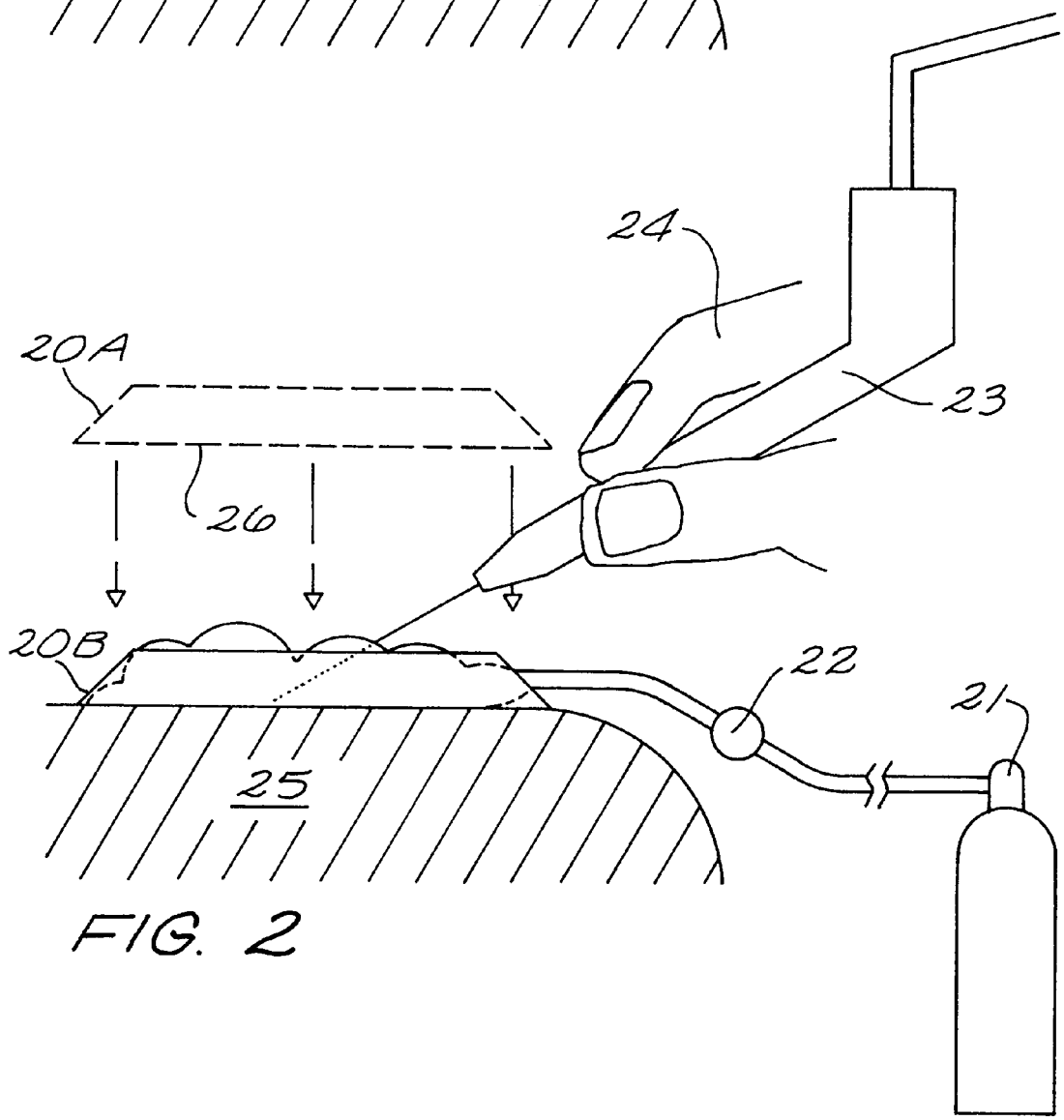
FIG. 2 is a side view of an alternative embodiment of the invention in which a container is used to contain the inert gas during the surgical procedure.

FIG. 2 is a side view of an alternative embodiment of the invention in which a container is used to contain the inert gas during the surgical procedure.

In this embodiment, a basin or retainer wall 20A and 20B is used to maintain the inert or noble gas around the surgical site. Basin 20A/20B is preferably ring shaped with an adhesive positioned on its lower edge 26. When Basin 20A is pressed against patient 25 to encompass the surgical site, the adhesive on the lower edge secures and seals basin 20B to patient 25.

Using valve 22, surgeon 24 is able to fill the interior of basin 20B with the inert gas from reservoir 21. Once the interior of basin 20B is filled, and the oxygen therein has been evacuated, surgeon 24, using laser 23, is able to treat the skin disorder.

This embodiment is particularly well suited for the situation where the surgeon desires to maintain the inert gas around the site and not allow it to readily escape from the site. In this embodiment, the preferred inert gas is argon.

Figure 3:
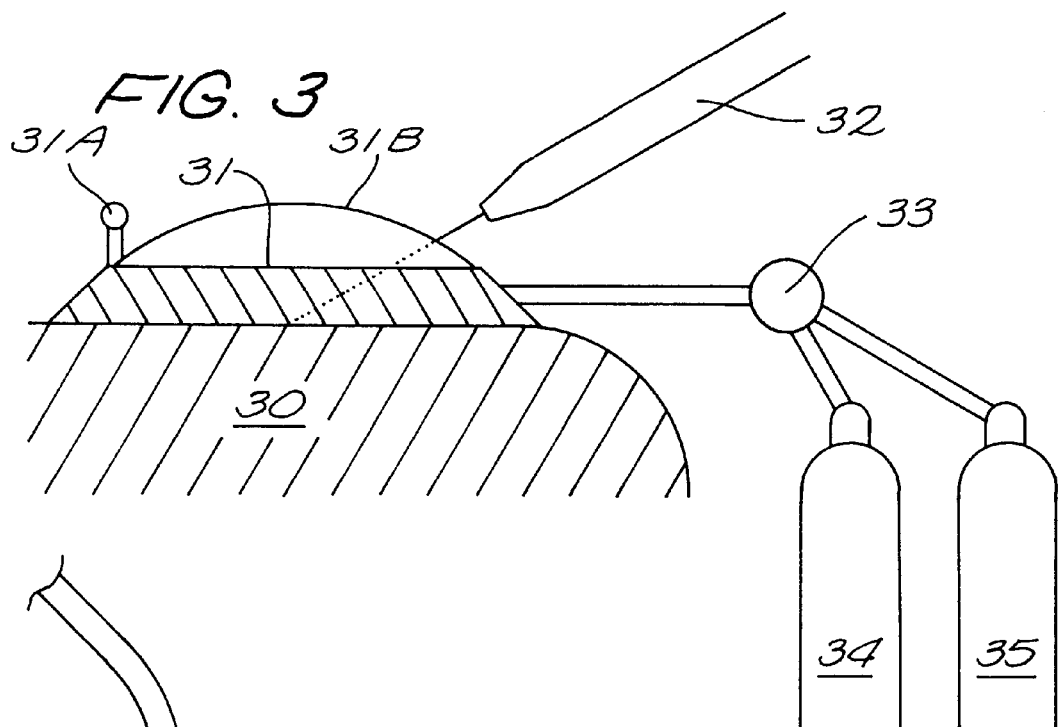
FIG. 3 is a side view of an alternative embodiment of the invention in which the surgical site is encapsulated and two forms of gas are used on the surgical site.

FIG. 3 is a side view of an alternative embodiment of the invention in which the surgical site is encapsulated and two forms of gas are used on the surgical site.

In this embodiment, capsule 31 is positioned over the surgical site. Capsule 31 is secured to patient 30 using an adhesive as discussed before. Capsule 31 seals the surgical site window 31B. Window 31B is composed of a material which allows the surgeon to view the surgical site and also allows a laser beam from laser 32 to be transmitted therethrough to the surgical site.

Capsule 31 is first filled with argon gas 34, or alternatively helium, via surgeon controlled valve 33. Vent 31A allows capsule 31 to be properly filled. The surgical procedure is then performed in an oxygen free or lean environment to obtain the desired affects.

To properly vent the small amount of smoke that is generated, a continuous flow of gas from reservoir 34 keeps the interior of capsule 31 clear.

Once the surgical procedure is completed, gas from reservoir 35 is injected via valve 33 into capsule 31. Gas within reservoir 35 is adapted to assist in the healing process and includes a variety of compositions well known to those of ordinary skill in the art including: an oxygen rich gas, a gas containing an anti-bacterial mist, and sterile air.

This embodiment permits the use of helium as an inert gas since it is fully contained at the site. Further, the use of two different gases (one inert and one for healing) permits the surgeon to fully treat the site and avoid the risk of secondary infections.

Figure 4:
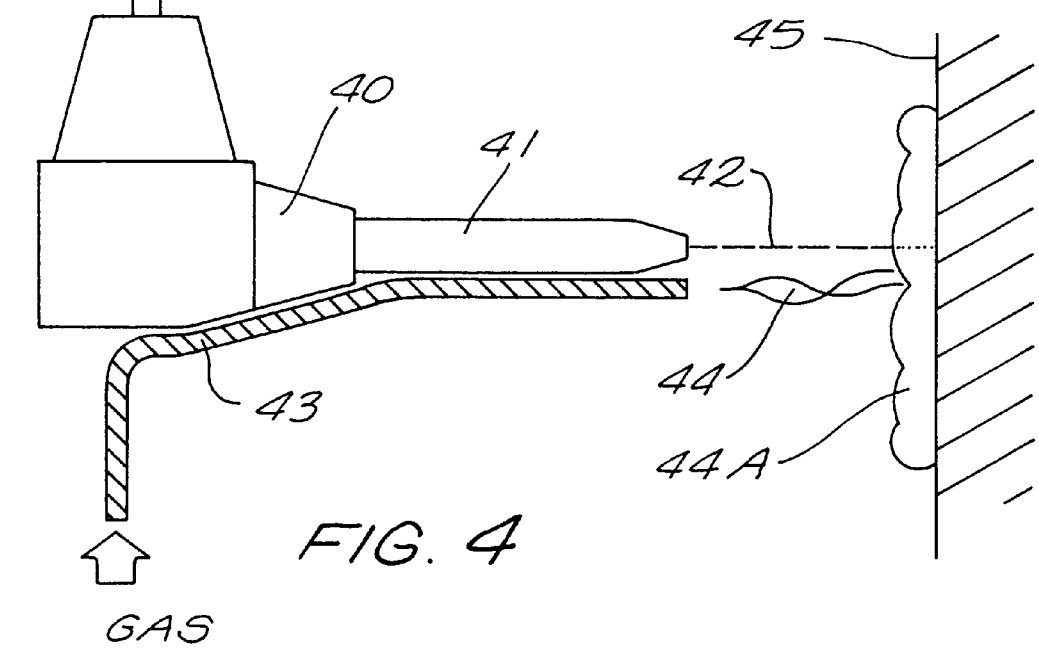
FIG. 4 is a side view of a handheld embodiment of the invention in which the inert gas is dispensed from the handheld capsule.

FIG. 4 is a side view of a handheld embodiment of the invention in which the inert gas is dispensed from the handheld capsule.

Laser 40 includes hand grip 41 from which laser beam 42 is emitted. Tubing 43 is secured to the housing of laser 40 and directs a flow of inert gas 44 parallel to laser beam 42.

As inert gas 44 contacts patient 45, the impact causes the inert gas to "mushroom" over the surgical site as illustrated 44A. This mushrooming affect, forces the oxygen away from the surgical site so that laser beam 42 is treating the skin of patient 45 in an oxygen free/lean environment to obtain the results outlined above.

FIG. 5A, 5B, and 5C are various views of an alternative handheld embodiment in which the reservoir of inert gas is secured in the handheld embodiment.

Referring to FIG. 5A, housing 50 is adapted to both apply the inert gas and also to direct the laser beam. In this embodiment, the inert gas is contained within a small canister 53 which is secured into housing 50 using cap 54A and threaded receptacle 54B. When canister 53 is fasten within housing 50 by cap 54A, the pressure applied during this operation causes a bayonet (not shown) to pierce canister 53, thereby making the inert gas available.

As the surgeon depresses trigger 52, the inert gas is communicated via extension 57 to exit via end 51. Once the inert gas has been provided to the surgical site (not shown), further depression of trigger 52 causes the laser to be activated to emit the laser beam.

End 51 is best illustrated in FIG. 5B. The laser beam is emitted via opening 55. Positioned around opening 55 (the laser beam) are in this embodiment, four orifices 56 through which the inert gas from canister 53. In this manner, the laser beam is encircled by flowing inert gas to assure that the surgical site is totally bathed in the inert gas.

As shown in FIG. 5C, laser beam 58 is contained within inert gas flow 59.

It is clear that the present invention creates a highly improved technique and apparatus for the laser treatment of skin conditions.

What is claimed is:

1. A system for resurfacing skin comprising:
    a) a laser adapted to emit a laser beam against a skin site of a patient; and,
    b) a bathing means for immersing the skin site in an oxygen replacing gas;
    wherein said bathing means includes a containment mechanism securable to the skin of the patient and adapted to encircle said skin site, and wherein said containment mechanism encapsulates said skin site, said containment mechanism having a laser permeable window therein.

2. A system according to claim 1, further including a reservoir containing said oxygen replacing gas, said reservoir communicating said oxygen replacing gas into said containment mechanism.

3. The system according to claim 2, further including a surgeon activated valve adapted to communicate said oxygen replacing gas to said containment mechanism.

4. The system according to claim 1, further including means for replacing said oxygen replacing gas in said containment mechanism with a gas adapted to encourage healing.

5. The system according to claim 4, wherein said gas adapted to encourage healing includes an oxygen rich gas.

6. The system according to claim 1, further including a surgeon activatable switch adapted to operate said laser and said bathing means.

7. The system according to claim 6, wherein said surgeon activatable switch includes means, upon activation by said surgeon, for initially activating said bathing means prior to activating said laser.

8. The system according to claim 1, wherein said oxygen replacing gas is chosen from the noble gases.

9. The system according to claim 8, wherein said oxygen replacing gas includes argon.

10. A skin treatment combination comprising:

a) a reservoir of noble gas;

b) a bathing apparatus adapted to bathe a surgical site with noble gas from said reservoir; and, c) a hand-held laser selectively emitting a laser beam at a selected intensity against said surgical site;

wherein said bathing apparatus includes a containment mechanism having a laser permeable window, said containment mechanism being securable and sealable to skin of the patient and adapted to encapsulate said skin site.

11. The skin treatment combination according to claim 10, further including means for replacing said noble gas in said containment mechanism with a gas adapted to encourage healing.

12. The skin treatment combination according to claim 11, wherein said gas adapted to encourage healing is an oxygen rich gas.

13. The skin treatment combination according to claim 10, further including means for providing said noble gas from said reservoir to said bathing apparatus under pressure above ambient conditions.

14. A surgical apparatus comprising a body member adapted to be grasped by a surgeon, said body member having attached thereto:

a) a reservoir of noble gas;

b) a bathing apparatus adapted to bathe a surgical site with noble gas from said reservoir;

c) a laser selectively emitting a laser beam at a selected intensity against said surgical site; and, d) a surgeon-operatable switch adapted to activate said bathing apparatus and said laser, wherein said bathing apparatus includes a containment mechanism having a laser permeable window, said containment mechanism being securable and sealable to skin of the patient and adapted to encapsulate said skin site.

15. The surgical apparatus according to claim 14, wherein said surgeon-activatable switch includes means for activating said bathing means prior to activating said laser.

\* \* \* \* \*